US009814840B2

(12) United States Patent
Cowe et al.

(10) Patent No.: US 9,814,840 B2
(45) Date of Patent: Nov. 14, 2017

(54) INJECTION DEVICES (75) Inventors: Toby Cowe, Oxford (GB); Jeremy Marshall, Oxford (GB)

(73) Assignee: OWEN MUMFORD LIMITED, Oxford (GB)

( * ) Notice: Subject to any disclaimer, the term of this patent is extended or adjusted under 35 U.S.C. 154(b) by 1241 days.

(21) Appl. No.: 13/878,479

(22) PCT Filed: Sep. 19, 2011

(86) PCT No.: PCT/GB2011/051754
§ 371 (c)(1),
(2), (4) Date: Apr. 9, 2013

(87) PCT Pub. No.: WO2012/049468
PCT Pub. Date: Apr. 19, 2012

(65) Prior Publication Data
US 2013/0197442 A1 Aug. 1, 2013

Related U.S. Application Data (60) Provisional application No. 61/394,896, filed on Oct. 20, 2010.

(30) Foreign Application Priority Data
Oct. 14, 2010 (GB) .................................. 1017363.1

(51) Int. Cl.
*A61M 5/50* (2006.01)
*A61M 5/32* (2006.01)
(Continued)

(52) U.S. Cl.
CPC .............. *A61M 5/321* (2013.01); *A61M 5/20* (2013.01); *A61M 5/2033* (2013.01);
(Continued)

(58) Field of Classification Search
CPC .. A61M 2205/3515; A61M 2005/3247; A61M 5/3243; A61M 5/3257; A61M 5/326; A61M 2005/3263; A61M 2005/3264
See application file for complete search history.

(56) References Cited

U.S. PATENT DOCUMENTS 4,108,177 A    8/1978   Pistor
5,360,410 A   11/1994   Wacks
(Continued)

FOREIGN PATENT DOCUMENTS

DE    197 31 778 A1    2/1999
EP         0518416 A1   12/1992
(Continued)

OTHER PUBLICATIONS

JP Office Action, dated Jul. 14, 2015; Application No. 2013-533277.
(Continued)

*Primary Examiner* — Nathan R Price
*Assistant Examiner* — John Doubrava
(74) *Attorney, Agent, or Firm* — Young & Thompson (57) ABSTRACT

An injection device includes an elongate housing (10), a syringe (12) disposed in the housing, and an internal piston (20) to express a dose from a needle (16) at its front end. The injection device further includes a shroud element (24) movable forwardly relative to the syringe to shroud the needle after use and a latch (74) movable between a latched state in which it restricts rearward movement of the shroud element, and a release state. The latch is moved to its latch state by a magnetic force (56).

10 Claims, 6 Drawing Sheets

(51) Int. Cl.
*A61M 5/20* (2006.01)
*A61M 5/315* (2006.01)

(52) U.S. Cl.
CPC .... *A61M 5/31501* (2013.01); *A61M 5/31511* (2013.01); *A61M 5/326* (2013.01); *A61M 5/3202* (2013.01); *A61M 5/3204* (2013.01); *A61M 2005/206* (2013.01); *A61M 2005/2073* (2013.01); *A61M 2005/3247* (2013.01); *A61M 2205/3515* (2013.01)

(56) References Cited

U.S. PATENT DOCUMENTS

| | | | |
|---|---|---|---|
| 2002/0156426 A1* | 10/2002 | Gagnieux | A61M 5/326 604/197 |
| 2005/0247558 A1* | 11/2005 | Anex | A61M 5/14248 204/275.1 |
| 2007/0005021 A1 | 1/2007 | Kohlbrenner et al. | |
| 2007/0191758 A1 | 8/2007 | Hunter et al. | |
| 2008/0086089 A1* | 4/2008 | Isaacson | A61M 5/3273 604/164.08 |
| 2010/0137808 A1 | 6/2010 | Wilmot et al. | |
| 2010/0211013 A1* | 8/2010 | Dillard, III | A61M 5/3257 604/164.08 |

FOREIGN PATENT DOCUMENTS

| | | | |
|---|---|---|---|
| GB | 686343 A | 1/1953 | |
| GB | 2342047 A | 4/2000 | |
| JP | 2007007401 A | 1/2007 | |
| JP | 2010532189 A | 10/2010 | |
| JP | 2012509717 A | 4/2012 | |
| WO | 00/15280 A1 | 3/2000 | |
| WO | 03/039635 A2 | 5/2003 | |
| WO | 2005/002653 A1 | 1/2005 | |
| WO | 2006/045215 A1 | 5/2006 | |
| WO | 2006/062983 A1 | 6/2006 | |
| WO | 2007/114934 A2 | 10/2007 | |
| WO | 2008/008206 A2 | 1/2008 | |
| WO | 2009007229 A1 | 1/2009 | |
| WO | 2009063030 A1 | 5/2009 | |
| WO | 2009/158145 A2 | 12/2009 | |
| WO | 2010068415 A1 | 6/2010 | |
| WO | 2010-076569 | 7/2010 | |

OTHER PUBLICATIONS

British Search Report, dated Dec. 22, 2010, from corresponding British application.
British Search Report, dated Feb. 2, 2011, from corresponding British application.
International Search Report, dated May 14, 2012, from corresponding PCT application.
Aug. 21, 2017, EP communication issued for related EP application No. 17162134.5.
Aug. 8, 2017, JP communication issued for related JP application No. 2016-199412.

* cited by examiner

INJECTION DEVICES

BACKGROUND OF THE INVENTION

Field of the Invention

This invention relates to injection devices and in particular, but not exclusively, to injection devices of the type where a syringe is disposed in an elongate housing and a shroud element moves forwardly relative to the syringe after use to shroud the needle and thereby minimise the risk of accidental needle stick injuries.

It is important for the latching mechanism to be highly reliable and to have latch characteristics that do not alter significantly during long term storage, for example due to changes in spring characteristics, plastic creep etc, especially if the injection device is reusable. The prior art contains many examples of devices where the shroud element is latched out by snapping past a flexible plastic finger or the like. We have devised an alternative to such devices where a magnetic force is used to enable the latch.

BRIEF SUMMARY OF THE INVENTION

Accordingly, in one aspect, this invention provides an injection device comprising:
 an elongate housing;
 a syringe disposed in said housing and having an internal piston to express a dose from a needle at its front end;
 a shroud element movable forwardly relative to the syringe to shroud the needle after use;
 a latch movable between a latched state in which it restricts rearward movement of the shroud element, and a release state;
 wherein said latch is moved to its latch state by a magnetic force.

The manner in which the magnetic force is provided may vary widely from application to application. In one arrangement, where the syringe has a longitudinally movable plunger for driving the piston, the latch may be moved by a magnetic force acting between the latch (or a part associated therewith) and said plunger. In this arrangement, the arrival of the plunger at or near the end of its stroke can be used magnetically to drive the latch into its latched state by attraction or repulsion. In such arrangements, one of the plunger and the latch may be provided with a magnet or be magnetic, with the other having a ferro-magnetic portion. Alternatively, the plunger and the latch may each be provided with magnets either in poles together or poles apart orientation.

In one particular arrangement, the latch may be formed of a ferro-magnetic metal. Although the latch could be an element that shuttles back and forth between the latched and release states, in one particular arrangement, a rear end portion of the latch is anchored within the housing of the injection device and extends forwardly from said anchorage to provide a latch surface at a forward region thereof. The shroud element may take many forms, but may conveniently comprise a cylindrical portion telescopically movable relative to the housing.

Preferably at least a component of said magnetic force acting between the latch and said plunger is in a direction to assist forward urging of the piston towards the end of the stroke of the plunger.

The invention also extends more generally to injection devices in which certain actions during the injection phase are enabled, initiated, or enhanced utilising magnetic force A potential problem encountered in the design of injection devices is that the force needed to expel a dose at a uniform rate from a syringe can increase towards the end of the stroke due to a reduced siliconisation down the length of the internal bore of the syringe. In many spring-driven systems, the spring obeys Hooke's law so that the force generated decreases as it extends, thereby providing a lower force during the stroke, where an increasing force may actually be desirable. This issue can be partly addressed by the use of constant force springs but these are expensive and still do not provide compensation for the increasing force required. We have therefore developed an injection device in which the force applied to the piston towards the end of the stroke is enhanced by the addition of a magnetic force.

Accordingly, in another aspect, this invention provides an injection arrangement for injecting a dose, said arrangement comprising a syringe having an internal piston for expressing a dose from the forward end; drive means for urging the piston forwardly in the syringe to express a dose, and further including means for applying a magnetic force directly or indirectly to said piston to assist forward movement at least towards the end of the forward stroke of the piston.

In many injection devices the movement of a drive plunger is initially applied to the body of a syringe to move the syringe forward to extend the needle to penetrate an injection site, with the plunger restrained against forward movement relative to the syringe. Once the syringe has reached a predetermined forward position, the plunger is released to move relative to the syringe to urge the piston to express a dose. Various systems exist to effect this sequencing, with some being quite complex requiring intricate delatching mechanisms and consequently having a high component count with attendant high tooling and assembly costs. We have previously described in WO2005/002653 a device with a low component count which uses an "O" ring as a friction coupling. We have now developed a further design which does not employ friction and which still retains a low component count. Furthermore, once the coupling has yielded, there is little or no residual friction inherent in the coupling.

In this aspect, the invention provides a n injection device comprising:
 a housing;
 a syringe having a generally hollow cylindrical body with a needle at its forward end and a bore slideably receiving an internal piston for expressing a dose through said needle;
 the syringe being mounted within said body for movement between a rearward position and a forward limit position;
 a drive plunger releasable to move forwardly to move the syringe forwardly and then to express a dose;
 a magnetic coupling acting between the plunger and said syringe body for transmitting forward motion of the plunger to said syringe body but yielding as said syringe arrives at or near said forward limit position to allow a forward end of said plunger to urge said piston forwardly within the syringe bore to express said dose.

In this manner, once the magnetic coupling between plunger and the syringe body has yielded there is little or no friction or drag interaction between the plunger and said syringe body and so substantially all of the first of the plunger force is applied to the piston.

The magnetic coupling may take a variety of forms but typically may comprise a thrust member for engaging and urging said syringe forwardly, the thrust member being magnetically coupled to said plunger. Thus one of the thrust member and the plunger may include a magnetised portion and the other thereof may include a ferro-magnetic portion, or each of said thrust member and said plunger may include a magnetised portion.

Whilst the invention has been described above, it extends to any inventive combination set out above, or in the following description or drawings.

BRIEF DESCRIPTION OF THE DRAWINGS

The invention may be performed in various ways, and two embodiments thereof will now be described by way of example only, reference being made to the accompanying drawings, in which.

DETAILED DESCRIPTION OF THE PREFERRED EMBODIMENTS

Figures 1, 2:
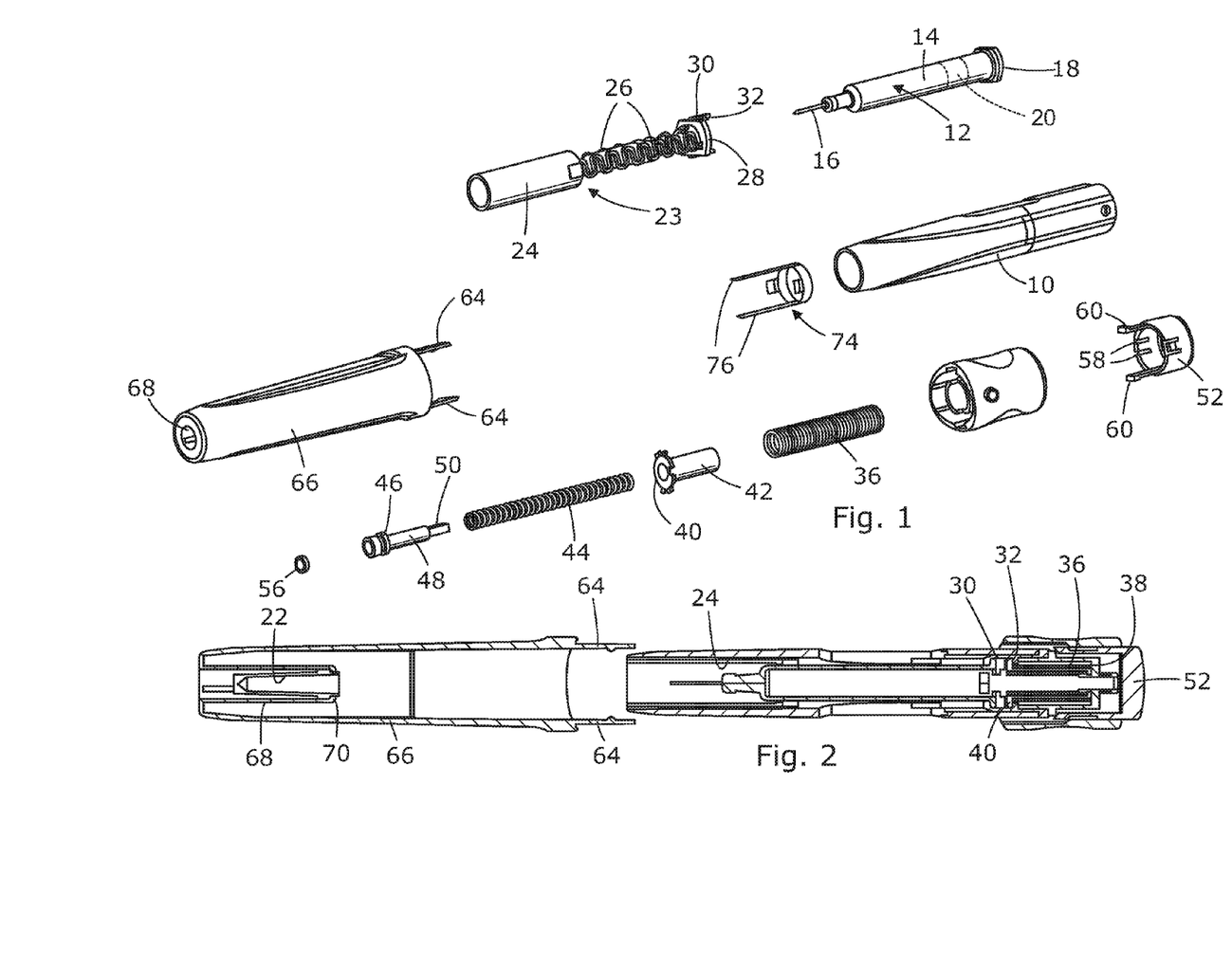
FIG. 1 is an exploded view of the first embodiment of an autoinjector in accordance with this invention.
FIG. 2 is a side section view through the autoinjector of FIG. 1 assembled and prior to use.
Figure 3A:
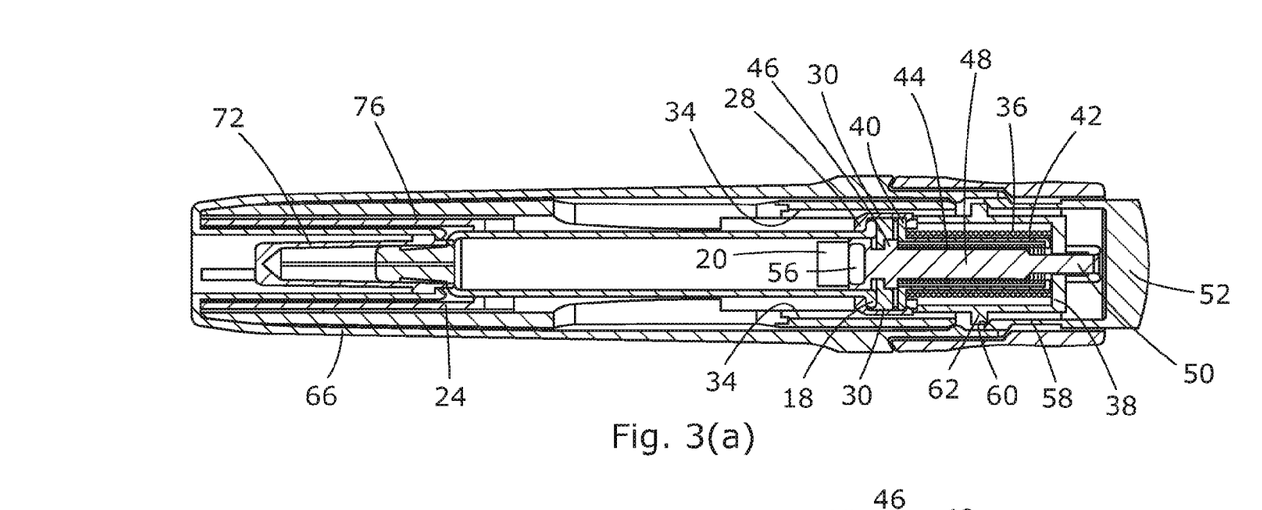
FIGS. 3(a) and (b) are respective side and top section views of the autoinjector with the cap in place, and removed.
Figure 3B:
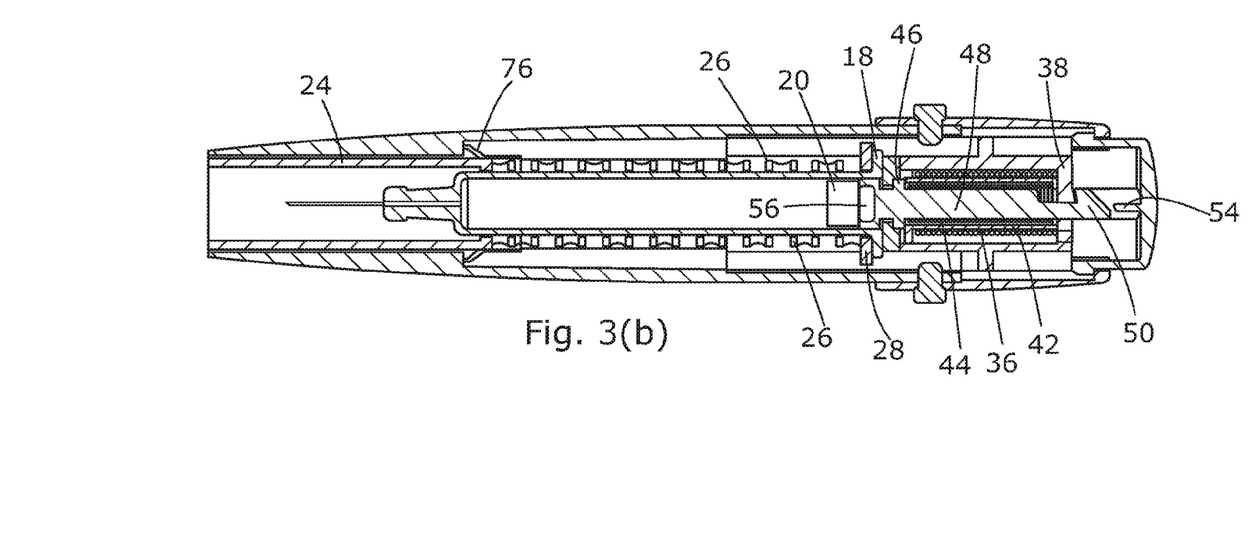

Referring initially to FIGS. 1 to 3, the autoinjector comprises an outer housing 10 of cylindrical form in the bore of which is disposed a syringe 12 of known form with a barrel 14, a needle 16 extending from the forward end, and a flange 18 at its rear end. A medicament is contained within the syringe and can be expressed through the needle by a piston 20 inside the barrel. The syringe is supported and surrounded by moulded plastics shroud/carrier 23 assembly comprising a forward hollow cylindrical portion 24 integrally formed with diametrically opposed springs 26 to either side, and a collar 28 adapted to engage the forward face of the syringe flange. Extending rearwardly from the collar are two diametrically opposed clearance fingers 30 with barbed teeth 32 that engage the intermediate member, as to be described below. In the pre-use position as shown in FIG. 3(a), the barbed fingers are prevented from outward splaying movement by the base of respective diametrically opposed grooves 34 on the inner surface of the rear part of the housing. In the pre-use position, the shroud portion 24 is telescopically received within the forward end of the housing and co-terminous therewith.

In the rear of the housing is provided a drive mechanism which comprises a first outer spring 36 which acts between the front face of a transverse inner wall 38 at the rear of the housing and a forward flange 40 of a top hat-shaped intermediate member 42. An inner, second, spring 44 is received within a cylindrical part of the intermediate member 42 and acts between an inner face of the rear end wall thereof and a circumferential rib 46 on the forward part of a plunger 48. At the rear end, the plunger has a resilient hooked arm 50 (see FIGS. 1, 3(b)) which latches around the edge of an aperture in the transverse inner wall 38 of the housing. Projecting rearwardly from the rear end of the housing is a captive axially slideable trigger button 52 movable against a rearward bias from the position shown in e.g. FIG. 3(b), where a release finger 54 is spaced rearwardly of the hooked arm 50, to a forward portion where the finger 54 cams the hooked arm to release its retention by the wall 38, thereby allowing the springs 36, 44 to drive the plunger 48 forwardly. The plunger is shaped and sized so that it can pass into and down the internal bore of the syringe barrel 14, to urge the piston 20 to express a dose. In the forward end of the plunger is a cylindrical recess in which is located a small powerful magnet 56.

The trigger button 52 is biased rearwardly by means of two integral forwardly extending sprung arms 58 with cam surfaces 60 which ride over respective abutments 62 inside the rear of the housing. However, initially, forward movement of the trigger button is prevented by means of two rearwardly extending locking arms 64 which extend back from the rear end of a cap 66. The cap covers the whole of the forward end of the housing and has a re-entrant cylindrical portion 68 with claw features 70. The claw features 70 slip over the rear end of a needle shield 72 which is secured to the front end of the needle during manufacture. Thus the cap 66 fulfils the functions of acting as a safety catch for the trigger button 52, serving as a shield remover. Anchored inside the forward end of the housing is a latch 74 formed of pressed steel or other ferro-magnetic material to provide two latch arms 76 which extend forwardly from an anchorage normally to sit in an annular space between the shroud 24 and an inner part of the housing wall.

Figure 4A:
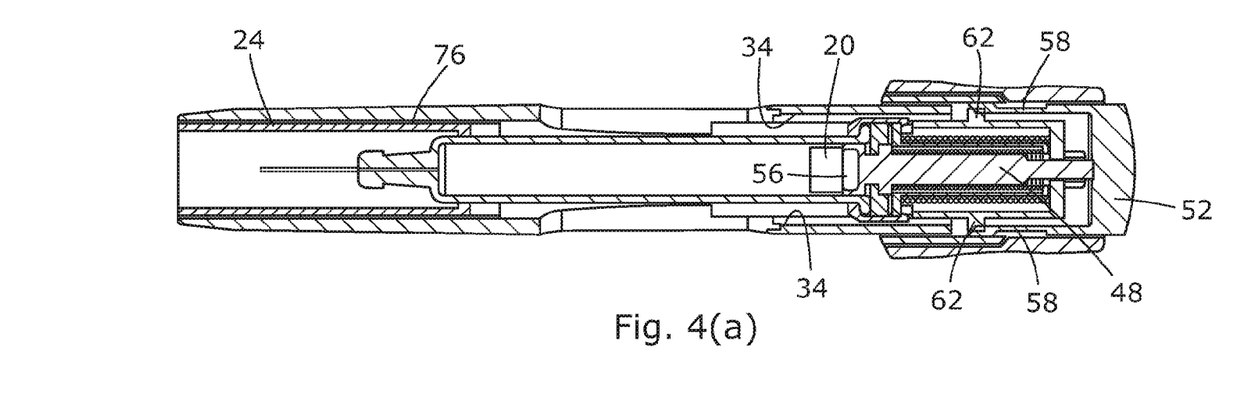
FIGS. 4(a) and (b) are respective side and top section views of the autoinjector with the firing button partially depressed immediately prior to the release of the plunger.
Figure 4B:
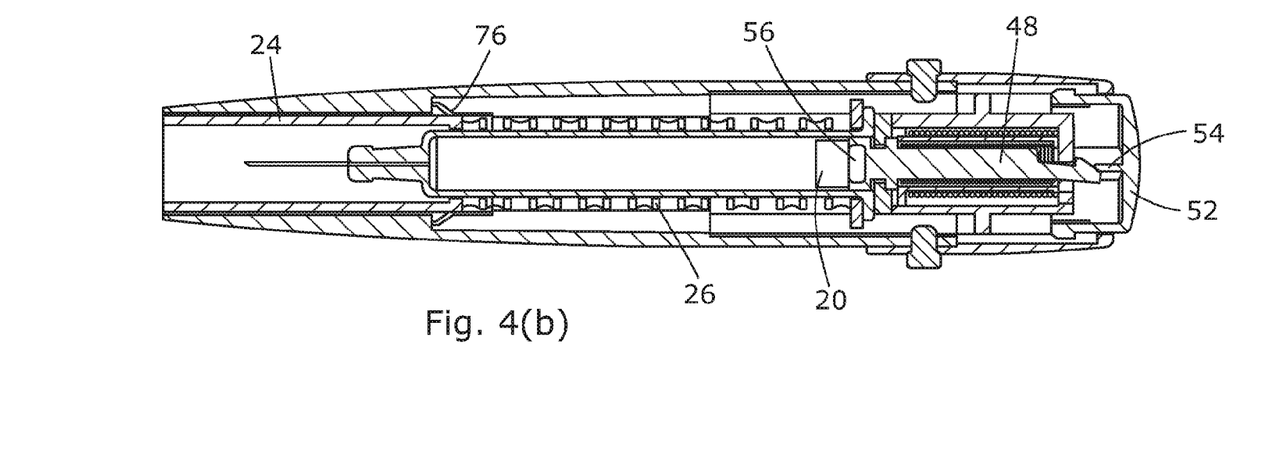
Figure 5A:
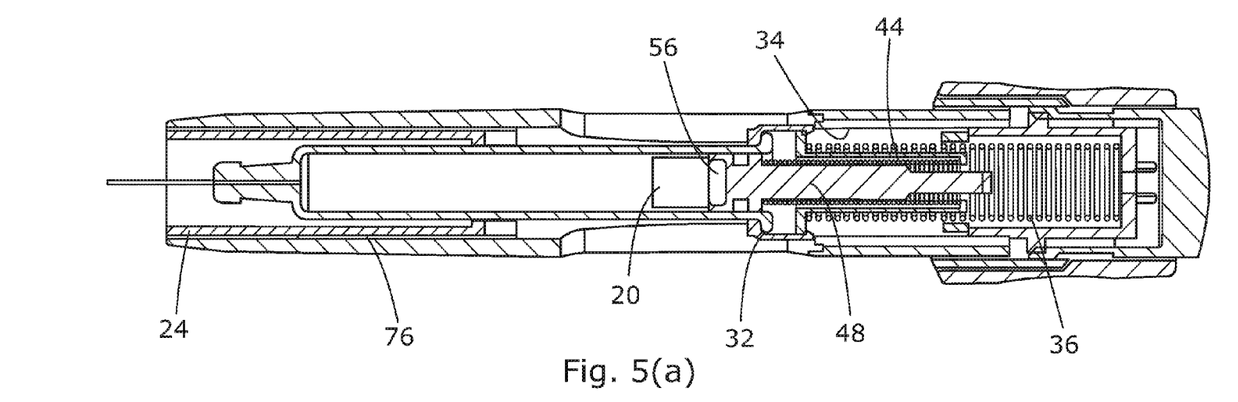
FIGS. 5(a), (b) and (c) are respective side section views showing the autoinjector with the syringe in its forwardmost position, shortly after breakout of the piston, and at the injection complete stage respectively.

In operation, the user pulls the cap 66 off forwardly which removes the needle shield 22 from the syringe and arms the device by rendering the trigger button 52 operational. The user then offers the injection device up to the injection site and presses the trigger button 52. This releases the hooked arm 50 of the plunger 48 as shown more particularly in FIG. 4(b). Once the plunger is released, the first spring 36 expands to extend the syringe 20 so that the needle penetrates the flesh. During this period (FIG. 5(a)), the second spring 44 remains substantially fully compressed, with the plunger 48 bearing against the piston 20 within the syringe but not moving it relative to the syringe. During the initial phase of penetration, the clearance fingers 32 on the syringe supporting collar 28 are constrained against outward splaying movement by the grooves 34 and so a gap is preserved between the syringe flange 18 and the flange 40 of the intermediate member 42, as long as the fingers are still in engagement with the constraining grooves.

Figure 5B:
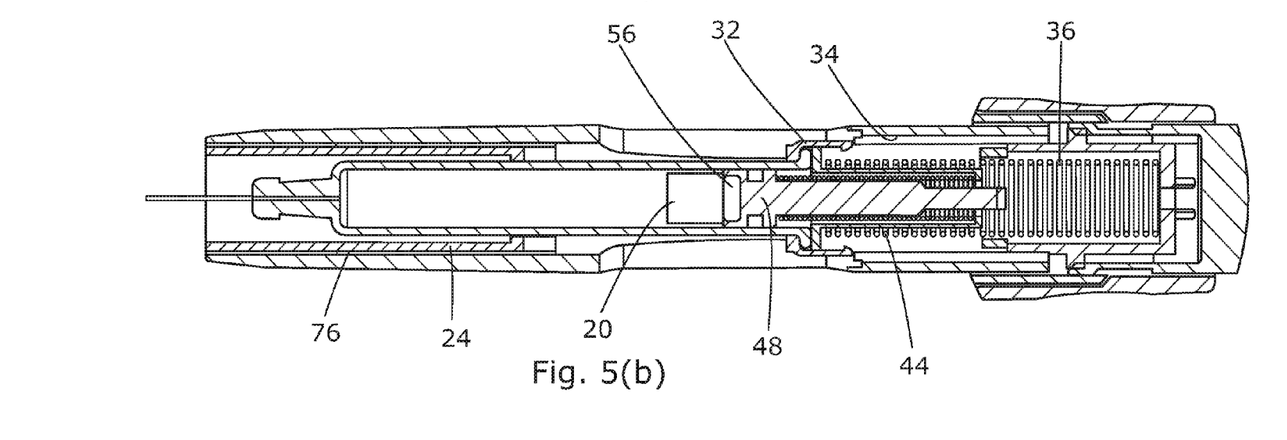
Figure 5C:
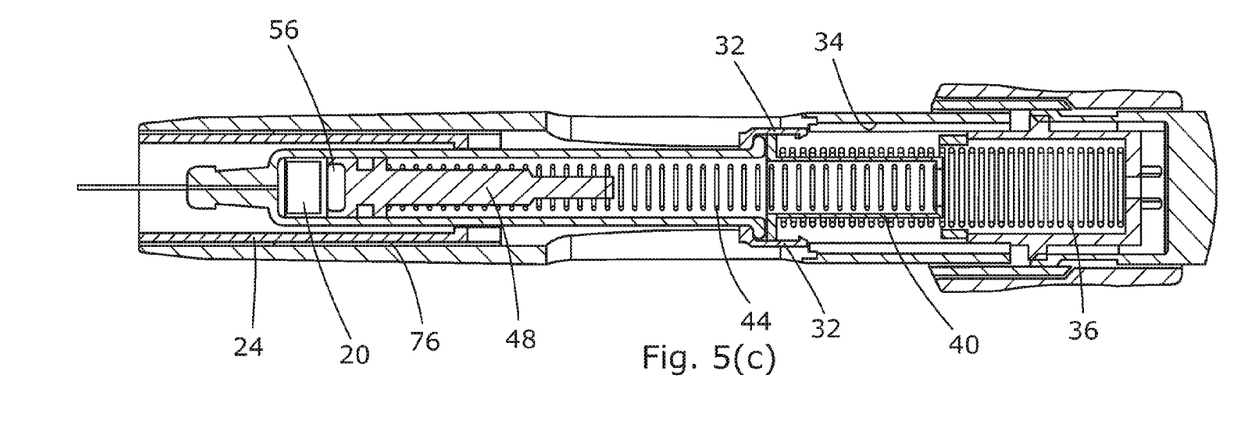
Figure 6:
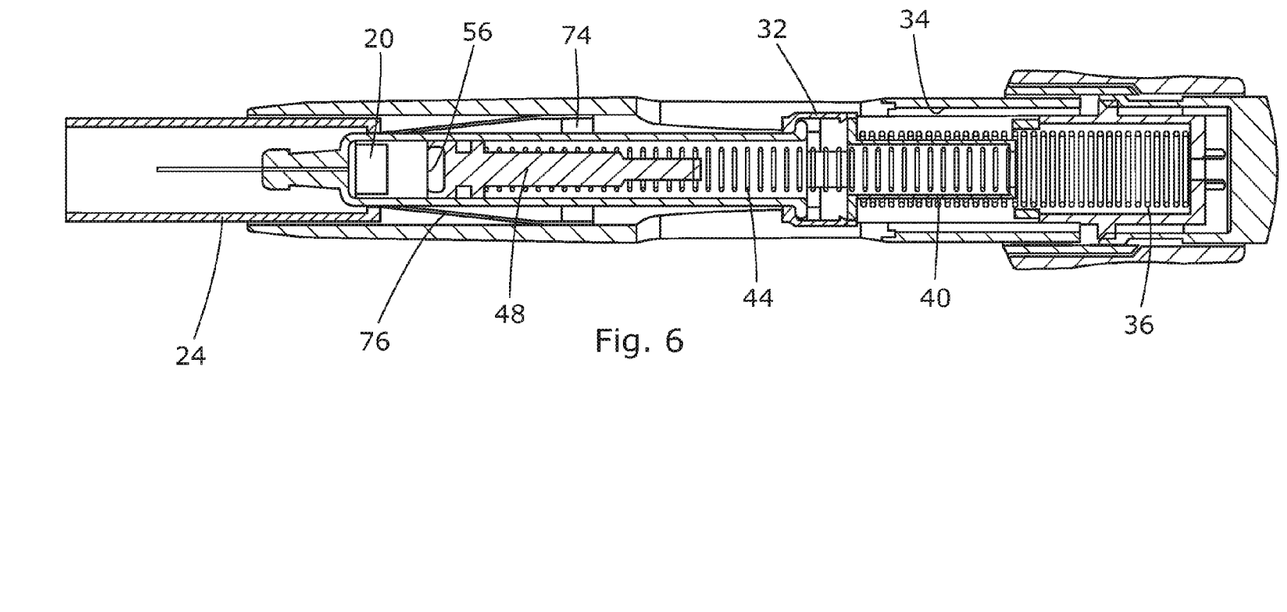
FIG. 6 is a view of the device after use, with the shroud extended and locked out by the magnetically enabled latch.

The fingers 32 exit the constraining grooves 34 at about the same time as forward movement of the syringe is arrested by the compression spring portions 26 bottoming out, the shroud 24 being held against movement by contact with the skin surface. When the syringe is arrested, the first spring 36 continues to expand to drive the flange 40 of the intermediate member into engagement with the syringe flange 18 thereby contributing to the force required to initiate movement of the piston down the syringe (FIG. 5(b)). From this position the second spring 44 expands to drive the piston down the barrel of the syringe to express a dose. At the end of its travel, it will be noted that the magnet 56 in the plunger is spaced between the latching arms 76 of the latch 74, as shown in FIG. 5(c). When the dose has been expressed, the user pulls the device away from the flesh and so the shroud portion 24 is free to expand under the influence of the compression spring portions 26. The shroud portion is driven by the springs 26 forwardly beyond the front tips of the latching arms 76. Once this happens, the latching arms are free to move inwardly to the latching positions shown in FIG. 6, under the influence of the magnet 20. The shroud portion 24 is therefore locked out and the device thereby rendered safe.

In other embodiments, not shown, one or more further magnets or ferro-magnet material may be disposed in the front end of the housing around or in front of the syringe in order to provide a magnetic boost effect as the plunger nears the end of its stroke. It will also be appreciated that the exact position of the magnet(s) and interacting components can be varied.

Figure 7:
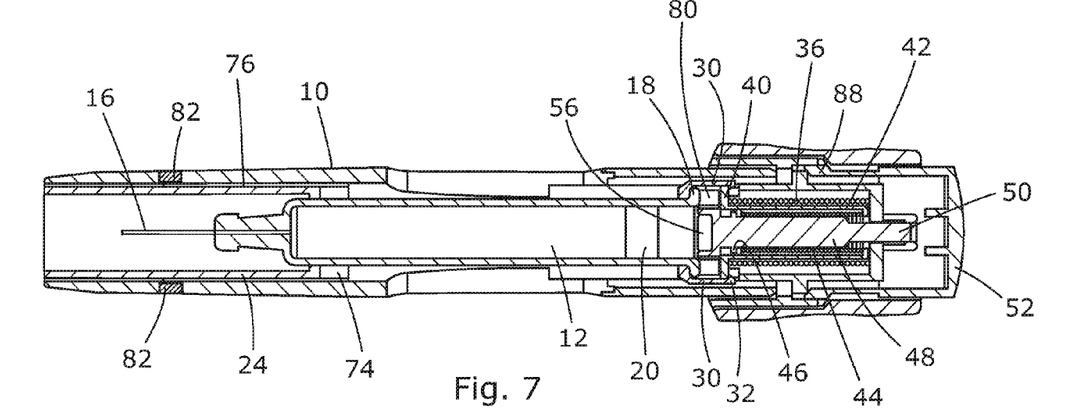
FIG. 7 is a side view through a second embodiment of an autoinjector.
Figure 8:
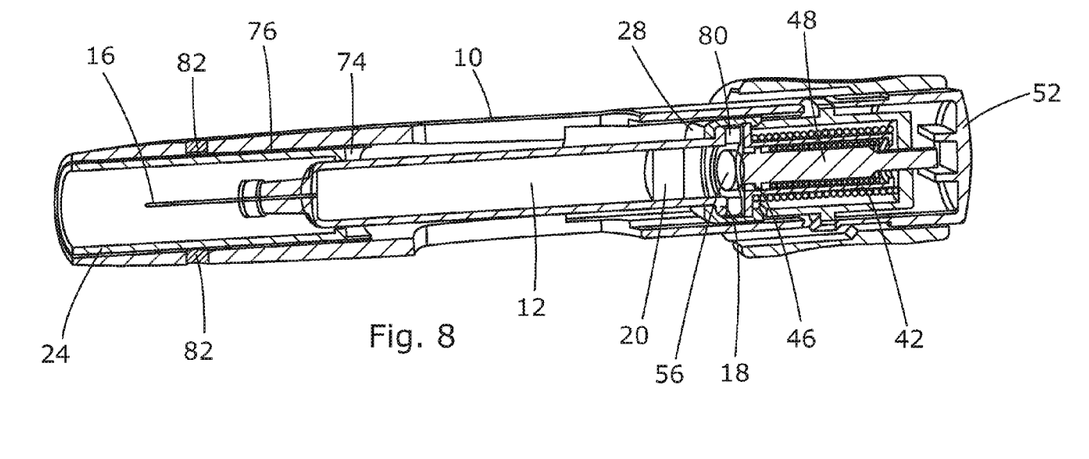
FIG. 8 is a shaded side view.

Referring now to FIGS. 7 and 8 the second embodiment has many of the same components as the first embodiment and which act in a similar fashion. These components are given the same reference numbers and will not therefore be described in detail again. This second embodiment incorporates a magnetic coupling embodiment between the plunger 48 and the syringe designed so that during an initial penetration phase of movement the plunger is coupled magnetically to a thrust collar 80 of ferro-magnetic material that is positioned in contact with the rear face of the syringe flange 18. Thus the plunger 48 and the syringe 18 are initially held against relative movement and so move as one during this phase, until the syringe is arrested by reaching its forwardmost position, with the needle inserted into the injection site. Upon arrest of the syringe, the spring force acting on the plunger overcomes the magnetic coupling force and the coupling yields so that the plunger is released to move forward relative to the syringe to move the plunger into contact with and to urge the piston forwardly to expel a dose. As previously, as the plunger moves alongside the ferro-magnetic latching arms 76 and they are attracted inwardly. This is enhanced in the embodiment by provision of two magnets 82 on the forward ends of the latching arms. These magnets are aligned so as to be attached towards and to exert a pull on the magnet 56 in the plunger to provide a magnetically influenced forward boost to the plunger toward the forwardmost end of its stroke. Upon completion of the injection and removal of the device from the site, the shroud 24 extends forwardly as the spring portions 26 re-expand, and as a rearward lip on the shroud passes the magnets, the latching arms move inwards to block retraction movement of the shroud and thereby lock it out. The magnets 82 may be housed slideably in through-holes in the housing wall, allowing them also to move inwards with the latching arms as the rearward lip on the shroud passes the magnets, and so provide a visual and tactile confirmation of locking out of the shroud 24.

The invention claimed is:

1. An injection device comprising: an elongate housing (10); a syringe (12) disposed in said housing and having an internal piston (20) to express a dose from a needle (16) located at a front end of the syringe; a shroud element (24) movable forwardly relative to the syringe to shroud the needle after use; a latch (74) movable between a latched state, in which the latch restricts rearward movement of the shroud element, and a release state; and a longitudinally movable plunger (48) for driving said piston, wherein one of the plunger (48) and the latch (74) comprises a magnetized portion, and the other of the plunger (48) and the latch (74) includes a ferro-magnetic portion, and wherein said latch (74) is urged to move into said latch state by a magnetic force (56), which arises from the magnetized portion and the ferro-magnetic portion, and acts between said latch (74) and said plunger (48).

2. The injection device according to claim 1, wherein said plunger (42) incorporates the magnetized portion (56), and said latch (74) includes the ferro-magnetic portion.

3. The injection device according to claim 1, wherein said latch (74) is anchored within the housing (10) at a rear end portion and extends forwardly to define a latch surface at a forward region.

4. The injection device according to claim 1, wherein said shroud element (24) comprises a cylindrical portion mounted for telescopic movement with the housing.

5. The injection device according to claim 1, wherein the shroud element (24) comprises a forward part of an integrally formed component including a spring portion (26) extending rearwardly from the shroud element and provided with a carrier portion (28) in which said syringe is received.

6. The injection device according to claim 1, wherein at least a component of said magnetic force acting between the latch (74) and said plunger (48) is in a direction that urges the piston (20) towards the end of the stroke of the plunger.

7. The injection device according to claim 1, wherein said latch (74) is anchored within the housing (10) at a rear end portion and extends forwardly to define a latch surface at a forward region.

8. The injection device according to claim 1, wherein said shroud element (24) comprises a cylindrical portion mounted for telescopic movement with the housing.

9. The injection device according to claim 1, wherein the shroud element (24) comprises a forward part of an integrally formed component including a spring portion (26) extending rearwardly from the shroud element and provided with a carrier portion (28) in which said syringe is received.

10. The injection device according to claim 1, wherein at least a component of said magnetic force acting between the latch (74) and said plunger (48) is in a direction to assist forward urging of the piston (20) towards the end of the stroke of the plunger.

* * * * *